United States Patent [19]

Massë

[11] Patent Number: 5,002,767

[45] Date of Patent: Mar. 26, 1991

[54] THERAPEUTIC COMPOSITION CONTAINING ALPHA-LINOLENIC ACID AND A COMPOUND CAPABLE OF PROMOTING THE PASSAGE OF THE ACID THROUGH THE CELL MEMBRANE, PLANT EXTRACT COMPRISING THE ACID AND THE COMPOUND, AND PROCESS FOR THE PREPARATION OF THE EXTRACT

[75] Inventor: Jean-Pierre Massë, Montpellier, France

[73] Assignee: Laboratories Natura Medica, Domazan, France

[21] Appl. No.: 229,171

[22] PCT Filed: Nov. 6, 1986

[86] PCT No.: PCT/FR86/00376

§ 371 Date: Aug. 24, 1988

§ 102(e) Date: Aug. 24, 1988

[87] PCT Pub. No.: WO88/03406

PCT Pub. Date: May 19, 1988

[51] Int. Cl.$^5$ .................. A61K 35/78; A61K 31/355; A61K 31/20
[52] U.S. Cl. .................. 424/195.1; 514/458; 514/558; 514/822; 514/863; 514/882; 514/886; 514/887; 514/930
[58] Field of Search .................. 424/195.1; 514/458, 514/558, 882, 886, 887, 863, 822, 930

[56] References Cited

FOREIGN PATENT DOCUMENTS 0115419 8/1984 European Pat. Off. .
1024518 2/1986 Japan .................. 514/458

OTHER PUBLICATIONS

Weissberger, Technique of Organic Chemistry, vol. III, Part I, Separation and Purification, pp. 302, 307, 817–823, 830–832, (1956).
Steinmetz, Codex Vegetabilis, 950–951, (1957).
Lust, The Herb Book, First Edition, p. 218, (1974).
"Unlisted Drugs", vol. 15, Jan. 1963, No. 1.
"Rote Liste", 1961, Verzeichnis pharmazeutischer Spezialpraparate.

*Primary Examiner*—John W. Rollins
*Attorney, Agent, or Firm*—Weingarten, Schurgin, Gagnebin & Hayes

[57] ABSTRACT

The invention relates to a therapeutic composition containing, as the active principle, α-linolenic acid and an alcohol of vegetable origin, such as a tocopherol or sitosterol. Preferably, the composition contains other fatty acids and is an organic extract of plants, especially of the Resedaceae family.

The invention also relates to the plant extracts as novel products.

The therapeutic composition is especially useful as an antiinflammatory.

3 Claims, No Drawings

THERAPEUTIC COMPOSITION CONTAINING ALPHA-LINOLENIC ACID AND A COMPOUND CAPABLE OF PROMOTING THE PASSAGE OF THE ACID THROUGH THE CELL MEMBRANE, PLANT EXTRACT COMPRISING THE ACID AND THE COMPOUND, AND PROCESS FOR THE PREPARATION OF THE EXTRACT

The invention concerns the field of drugs, especially antiinflammatories.

It relates to a therapeutic composition which contains, as the active principle, at least α-linolenic acid and at least one compound capable of promoting the passage of the acid through the cell membrane, in association with a physiologically acceptable excipient.

It further relates to the plant extracts containing the active principle.

α-Linolenic acid by itself has no therapeutic activity.

According to the present invention, it has been found that the active principle described above has totally unexpected therapeutic properties, especially antiinflammatory properties. Alcohols of vegetable origin, such as tocopherols ($\alpha$, $\beta$, $\gamma$ and $\delta$) or sitosterols like β-sitosterol, may be mentioned among the compounds which are capable of promoting the passage of α-linolenic acid through the cell membrane. Apart from these two types of product, the active principle can contain other compounds, especially $C_{16}$ and $C_{18}$ fatty acids such as palmitic acid, stearic acid, oleic acid and linoleic acid. Moreover, the presence of these other compounds often results from the process for the preparation of the active principle, as will be understood below.

Thus, preferably, the active principle will have the following composition in percentages by weight:

| | |
|---|---|
| ζ-linolenic acid | 10–80 and preferably 15–60 |
| compound | 10–80 and preferably 15–60 |
| $C_{16}$ and $C_{18}$ fatty acids other than ζ-linolenic acid | 0–65 and preferably 15–55 |

The active principle is preferably an aqueous or organic extract of plants which contain α-linolenic acid and a compound capable of promoting the passage of the acid through the cell membrane.

The expression "aqueous or organic extract" refers to the product which results from the action of an aqueous or organic solvent on ground plants, i.e. the process involves extracting the products which are soluble or miscible in these solvents.

Among the plants which are suitable for the present invention, preference will be given to those belonging to the Resedaceae family, such as *Reseda lutea, Reseda luteola, Reseda glauca* L., *Reseda suffruticosa, Reseda alba, Reseda jacquini* Rehb, *Reseda odorata, Reseda complicata, Reseda bory,* and *Reseda phyteuma.*

It is possible to use the whole plants harvested when flowering or fruiting, or seeds. They are then dried in the absence of light under a stream of air.

The aqueous extract advantageously results from extraction of ground plants or seeds with water, followed by recovery of the dry solute by an appropriate means.

Appropriate means which may be used are lyophilization or nebulization (after the addition, in the latter case, of an agent for imparting viscosity or an adsorbent, such as hydroxypropyl methyl cellulose (HPMC) or silicic acid).

It is also possible to extract the resulting aqueous solution with an organic solvent and then to concentrate the organic phase and finish, if appropriate, with a chromatographic fractionation of the concentrate. Advantageously, the fractionation will be such as to enable the fractions containing the fatty acids to be recovered. Preferably, the aqueous extract will result from a solid-liquid chromatographic fractionation, the eluent being a 50/50 benzene/methanol mixture, the support being silica and elution being carried out in 10 ml fractions, and from recovery of the fractions between forty-three and sixty.

The organic extract results from extraction of ground plant or seeds with an organic solvent such as ether, hexane or methanol, or with liquid $CO_2$ in the supercritical phase, followed by recovery of the dry solute by evaporation. However, preferred solvents will be ether, hexane or petroleum ether and especially methyl tert-butyl ether, or liquid $CO_2$ in the supercritical phase, either in the pure state or, if appropriate, with traces of water, ethanol or the like (to extract the compounds of greater or lesser polarity).

It must be emphasized that all the plant extracts are novel and the applicant is claiming them as novel products characterized by the process for their preparation, as follows from the foregoing description.

The therapeutic compositions according to the invention have proved useful as antiinflammatories, antihistamines, agents for inhibiting hemorrhoids, agents for inhibiting varicose veins, anticoagulants, vasoconstrictors or agents for inhibiting psoriasis.

The concentration of the extract in the finished product is advantageously between 10 and 25% by weight in the case of the aqueous extract and 2 to 12% in the case of the organic extract.

The product can be administered locally (ointment, cream, spray, lotion, gel), intradermally (ampoules or with the aid of conventional excipients) or by the general oral or parenteral route (capsules, drops to be taken orally, etc.).

The invention is now illustrated by particular non-limiting Examples.

PREPARATION OF THE EXTRACTS

Example 1: Preparation of the Aqueous Extract

The plant is pulverized with a roller mill until a fairly coarse powder is obtained. The resulting powder is extracted with 8 times its weight of distilled water at a temperature of 70° C. for 8 h, with mechanical agitation.

The extract obtained after filtration and expression of the pulp is dried by nebulization or lyophilization.

Nebulization is carried out after the addition of hydroxypropyl methyl cellulose (HPMC).

Example 2: Preparation of the Aqueous Extract (2nd method)

The aqueous extract of Example 1 is precipitated with 95° ethanol to give a mixture of fatty substances.

Example 3: Preparation of the Aqueous Extract (3rd method)

Starting from the aqueous phase obtained according to Example 1, and instead of lyophilization or nebulization, the solute is extracted with ether in a separating funnel. The ether phase is concentrated under reduced pressure until a green oil is obtained. This extract is then fractionated on a silica column using a 50/50 benzene/methanol mixture as the eluent. 10 ml fractions are collected. As from fraction 45, the solution only contains fatty acids up to fraction sixty. Fractions 45 to 60 are combined.

Example 4: Preparation of the Ether Extract

The operation was carried out on the whole plant or on the seeds.

1 kg of plant is extracted by maceration with 6 l of organic solvent (ether, petroleum ether and especially hexane) for 48 h at room temperature, with mechanical agitation.

After filtration on paper, the resulting solution is concentrated under reduced pressure until an oily extract is obtained, which is dried under a stream of nitrogen.

The ether extract has the following chemical composition (in percentages by weight) with a 10% margin of error:

| | |
|---|---|
| d,l-$\zeta$-tocopherol | 18 |
| $\beta$-sitosterol | 18 |
| palmitic acid | 13.5 |
| stearic acid | 1 |
| oleic acid | 8 |
| linoleic acid | 10 |
| $\zeta$-linolenic acid | 31.5 |

NB: This extract must be stored in the absence of light and in a cool place.

Example 5: Preparation of the Alcohol Extract

The operation is carried out under the same conditions as for Example 4, except that methanol is taken as the solvent.

Pharmacological Properties

The antiinflammatory activity of the extracts of Reseda Phyteuma obtained according to Example 1 to 5 was evaluated by general administration, in comparison with a reference in Wistar rats and with the powerful antiinflammatory indomethacin, as the percentage reduction in the swelling of the back paw caused by the phlogogenic agent carrageenin. The results are collated in Table I on the following page.

TABLE I

| | Percentage reduction in swelling after | | | |
|---|---|---|---|---|
| | 2 h | 3 h | 4 h | 5 h |
| Reference | 33.70 | 34.40 | 24.02 | 29.45 |
| Indomethacin 5 mg/kg | 38.60 | 71.62 | 40.42 | 32.8 |
| Example 1 ① | 36 | 54.55 | 31.37 | — |
| 100 mg/kg ② | 49.73 | 41.22 | 22.47 | 7.83 |
| Example 2 | 42.83 | 41.42 | 27.40 | 12.40 |

TABLE I-continued

| | Percentage reduction in swelling after | | | |
|---|---|---|---|---|
| | 2 h | 3 h | 4 h | 5 h |
| 100 mg/kg Example 3 | 48.24 | 55.80 | 46.46 | 43.76 |
| 100 mg/kg Example 4 | 53.41 | 70 | 54.70 | 41.08 |
| 5 mg/kg Example 5 | 24.37 | 16.17 | — | — |
| 5 mg/kg | | | | |

① and ② correspond to two different groups of rats.

TOXICITY

A. Acute toxicity

This was determined on male rats of the Wistar strain and male mice of the Swiss strain using two modes of administration: oral and intraperitoneal.

$LD_{50}$ rat
   oral: $LD_{50}$ greater than 5 g/kg
   intraperitoneal: $LD_{50}$ greater than 2 g/kg $LD_{50}$ mouse
   oral: $LD_{50}$ greater than 5 g/kg
   intraperitoneal: $LD_{50}$ greater than 2 g/kg B. Local tolerance of the nebulizate and of the ether extract in the form of a 10% cream The local tolerance of the cream was assessed on Fauve de Bourgogne rabbits by the repeat cutaneous application of 2 g/kg of cream for 4 weeks to the animal's side, which had been shaved beforehand over an area of 80 cm.

The treatment did not influence the change in weight of our animals. The consumption of food and drinking water was identical in the control animals and treated animals.

The fur grew again normally.

Examination of the integuments showed a smooth and extremely supple skin.

In autopsy, examination and weighing of the following organs: liver, spleen, kidneys, testicles, adrenal glands, heart, thyroid and pituitary gland, showed no signs of toxicity. There was no apparent difference between control animals and treated animals.

Meticulous examination of the gastric and duodenal mucosa showed no anomalies.

Clinical Results

The tests were performed with the extract of Reseda Phyteuma of Example 1 in the form of a cream containing 10% by weight of organic extract.

The results collated in Table II on the following pages, which were recorded by doctors, are very satisfactory for external or internal hemorrhoids, whether or not accompanied by pruritus or slight fissures, for varicose veins and for insect bites.

The product is also an excellent emollient.

TABLE II

| Sex | Age | Diagnosis | Results | | Tolerance | Latency | Duration |
| | | | Doctor | Patient | | | |
|---|---|---|---|---|---|---|---|
| M | 36 | Thrombosis with external edema | B | B | B | 2 d | 15 d |
| M | 75 | Anal pruritus | B | B | B | 2 | 8 |
| M | 78 | Anusitis in a diarrheal subject | Average | Average | B | 10 | 10 |
| M | 48 | Thrombosis with edema | B | B | B | 1 | 8 |
| F | 43 | Attack of hemorrhoids | Not reviewed | | | | |

TABLE II-continued

| Sex | Age | Diagnosis | Doctor | Patient | Tolerance | Latency | Duration |
|---|---|---|---|---|---|---|---|
| M | 50 | Anusitis with painful bleeding | B | B | B | 2 | 15 |
| F | 59 | Painful superficial fissure | B | B | B | 5 | 15 |
| F | 75 | Hemorrhoids + circumanal mycosis | Average | Average | | | |
| F | 62 | Anusitis with bleeding | B | B | B | 3 | 15 |
| F | 57 | Chronic anal burning | B | B | B | Occasional use | |
| M | 36 | Internal hemorrhoids | B | B | B | Immediate | 10 |
| M | 51 | Anal pruritus + hemorrhoids | B | B | B | 2 | 15 |
| M | 36 | Anusitis + pruritus | Average | Average | | | |
| M | 49 | Hemorrhoidal inflammation + postoperative pruritus | B<br>B | B<br>B | B<br>B | 2<br>2 | 8<br>15 |
| F | 59 | Pain + inflammation after sclerosis | B | B | B | | 15 |

What is claimed is:

1. A method of treating inflamed tissue in human beings or animals comprising the step of administering by local, intradermal, oral or parenteral route, an effective amount of a therapeutically active composition having an active principle which consists essentially of an extract of plant tissue or seed of at least one plant of the Resedaceae family, said extract including alpha linolenic acid and promoting material which is effective to promote the passage of alpha linolenic acid across cell membranes, and being admixed with physiologically acceptable excipient.

2. A method of treating inflammatory events, histaminic disorders, or psoriasis, in human beings or animals, comprising the step of administering by local, intradermal, oral or parenteral route, an effective amount of a therapeutic composition comprising an extract of at least one plant or seeds of a plant belonging to the Resedaceae family containing simultaneously a therapeutically active amount of at least alpha-linolenic acid and of at least one promoting compound capable of promoting the passage of the acid through the cell membrane, in a physiologically acceptable excipient.

3. A method of treating hemorrhoids, disorders of coagulation or disorders in which a vasoconstriction is sought, in human beings or animals, comprising the stop of administering by local, intradermal, oral or parenteral route, an effective amount of a therapeutic composition comprising an extract of at least one plant or seeds of a plant belonging to the Resedaceae family containing simultaneously a therapeutically active amount of at least alpha-linolenic acid and of at least one promoting compound capable of promoting the passage of the acid through the cell membrane, in a physiologically acceptable excipient.

* * * * *